(12) United States Patent
Dupps et al.

(10) Patent No.: US 10,398,763 B2
(45) Date of Patent: Sep. 3, 2019

(54) CORNEAL STIFFENING FOR TREATING ASTIGMATISM

(71) Applicant: THE CLEVELAND CLINIC FOUNDATION, Cleveland, OH (US)

(72) Inventors: William J. Dupps, Bay Village, OH (US); Ibrahim Seven, Cleveland, OH (US)

(73) Assignee: THE CLEVELAND CLINIC FOUNDATION, Cleveland, OH (US)

( * ) Notice: Subject to any disclaimer, the term of this patent is extended or adjusted under 35 U.S.C. 154(b) by 1082 days.

(21) Appl. No.: 14/165,796

(22) Filed: Jan. 28, 2014

(65) Prior Publication Data

US 2014/0213525 A1 Jul. 31, 2014

Related U.S. Application Data

(60) Provisional application No. 61/757,425, filed on Jan. 28, 2013.

(51) Int. Cl.
*A61K 38/39* (2006.01)
*A61F 9/013* (2006.01)

(52) U.S. Cl.
CPC .............. *A61K 38/39* (2013.01); *A61F 9/013* (2013.01)

(58) Field of Classification Search
None
See application file for complete search history.

(56) References Cited

U.S. PATENT DOCUMENTS

| 6,537,545 | B1 * | 3/2003 | Karageozian | ......... A61F 9/0017 424/427 |
| 2009/0171305 | A1 * | 7/2009 | El Hage | ................... A61F 2/14 604/294 |

OTHER PUBLICATIONS

Bozkurt et al., Topographical analysis of corneal astigmatism in patients with tilted-disc syndrome, Cornea. Jul. 21, 2002;(5):458-62, Abstract only, 2 pages.*

* cited by examiner

*Primary Examiner* — Gigi G Huang
(74) *Attorney, Agent, or Firm* — Tarolli, Sundheim, Covell & Tummino LLP

(57) ABSTRACT

Methods are provided for treating astigmatism in an eye of a patient. An axis of greater curvature of the eye is determined. A stiffening process is applied to a cornea of the eye in a pattern defined from the axis of greater curvature of the eye.

1 Claim, 4 Drawing Sheets

CORNEAL STIFFENING FOR TREATING ASTIGMATISM

RELATED APPLICATION

This application claims priority from U.S. Provisional Application No. 61/757,425, filed 28 Jan. 2013, the subject matter of which is incorporated herein by reference in its entirety.

TECHNICAL FIELD

This invention relates to medical technologies, and more particularly, to use of a corneal stiffening to treat astigmatism.

BACKGROUND

Astigmatism is an optical defect in which vision is blurred due to the inability of the optics of the eye to focus a point object into a sharp focused image on the retina. This may be due to an irregular or toric curvature of the cornea or lens. The two types of astigmatism are regular and irregular. Irregular astigmatism is often caused by a corneal scar, ocuar laceration, corneal ectatic disease, or scattering in the crystalline lens, and cannot be corrected by standard spectacle lenses, but can be corrected or neutralized by certain contact lenses. The more common regular astigmatism can be corrected by eyeglasses or toric lenses. The refractive error of the astigmatic eye stems from a difference in degree of curvature refraction of the two different meridians. For example, the image may be clearly focused on the retina in the horizontal plane, but not in the vertical plane. Astigmatism causes difficulties in seeing fine detail resulting in blurred vision.

SUMMARY OF THE INVENTION

In accordance with an aspect of the present invention, a method is provided for treating astigmatism in an eye of a patient. An axis of greater curvature of the eye is determined. A stiffening process is applied to a cornea of the eye in a pattern defined from the axis of greater curvature of the eye.

In accordance with another aspect of the present invention, a method is provided for treating astigmatism in an eye of a patient. Each of an axis of greater curvature of the eye and at least one other optical parameter are determined. A stiffening process is applied to a cornea of the eye in a pattern defined from the axis of greater curvature of the eye and the at least one other optical parameter.

In accordance with yet another aspect of the present invention, a method is provided for treating astigmatism in an eye of a patient. Each of an axis of greater curvature of the eye and a magnitude of the astigmatism is determined. A first stiffening process is applied to a cornea of the eye in a pattern defined from the axis of greater curvature of the eye and an intensity of the stiffening process is determined from the magnitude of the astigmatism. The pattern is applied as to be substantially symmetrical around the axis of greater curvature. A second stiffening process is applied in a homogenous manner across substantially the entire cornea to stabilize the cornea after the first stiffening process.

DETAILED DESCRIPTION

In accordance with an aspect of the present invention, a treatment is provided for ocular astigmatism, for example, arising from corneal astigmatism or lenticular astigmatism, through patterned stiffening of the cornea. The method is applicable to any spatially tunable technique for corneal stiffening. The treatment can be curvature-guided, elevation-guided, and/or mechanical or optical property guided to provide customized corneal stiffening treatments for each patient. These treatments can be designed to homogenize curvature, elevation, or mechanical properties to reduce astigmatism as well as accompanying spherical ametropia.

Figure 1:
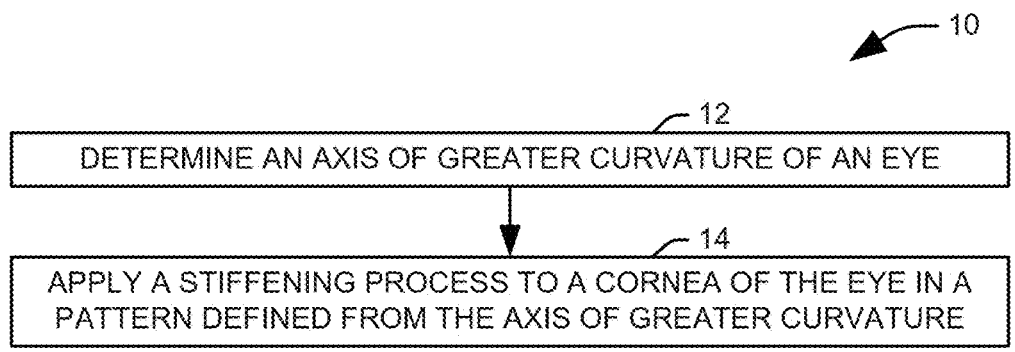
FIG. 1 illustrates a method of treating astigmatism in an eye of a patient in accordance with an aspect of the present invention.

FIG. 1 illustrates a method 10 of treating astigmatism in an eye of a patient in accordance with an aspect of the present invention. At 12, an axis of greater curvature of the eye is determined. In one implementation, at least the corneal region of the eye can be scanned, for example, via an appropriate imaging system, and the axis of greater curvature of the eye and one or more other optical parameters associated with the eye can be determined. The imaging component can utilize magnetic resonance imaging (MRI), optical coherence tomography (OCT), Scheinpflug imaging, or any other appropriate imaging modality. The determined images can be supplemented by additional values, such as a measured corneal topography and a determined axial length of the eye. To this end, the elastography imaging device can include, for example, an ultrasound imaging device or a partial coherence interferometer arrangement, for determining the axial length, as well as an appropriate imager for determining the corneal topography.

At 14, a first stiffening process is applied to a cornea of the eye in a pattern defined from the axis of greater curvature of the eye. For example, the stiffening process can include stiffening via riboflavin and ultraviolet light, rose bengal, genapin, nonenyzamic nitration with nitrite compounds, glyceraldehyde, glutaraldehyde, and other chemical or photochemical collagen stiffening techniques. In accordance with an aspect of the present invention, the pattern of the stiffening process can be arranged to be substantially symmetric to the axis of greater curvature. Alternatively, the pattern may be made deliberately asymmetric, for example, to allow for deliberately inhomogeneous effects used to treat complex astigmatic patterns. For example, asymmetric pattern widths, depths, and contours can be utilized, as well as, graded intensity treatments can be used to provide these effects.

In one example, the determined pattern can be varied according to other optical parameters, for example, a magnitude of the astigmatism. In another implementation, one of a set of standard patterns can be selected according to determined optical parameters, such as a determined spherical refractive error of the eye (e.g., myopia or hyperopia), and an intensity of the treatment can be varied with a magnitude of the astigmatism. In one implementation, a second stiffening process is applied in a homogenous manner across substantially the entire cornea to stabilize the cornea after the first, selective stiffening process In one implementation, the images of the eye can be digitized and processed as to obtain an overall geometry of the eye. For example, the images can be filtered and one or more edge detection algorithms can be utilized to determine the boundaries of the various tissue layers. Once the boundaries of the various tissue components is established, the processed image data can be provided to a finite element modeling (FEM) component that establishes a finite element model of the ocular tissue according to the determined geometry of the eye and one or more biomechanical parameters, which can include parameters such as Poisson's ratio and Young's modulus, as well as non-linear measures of elasticity, such as hysteresis, creep, stress relaxation, and a strain dependent function for Young's modulus, for each of the tissue types. An appropriate FEM modelling system is described in detail in U.S. Published Patent Application No. 2013/0138400, the entire contents of which are herein incorporated by reference.

One or more biomechanical parameters specific to the patient can be determined at a parameter measurement system. For example, the parameter measurement system can include an imaging system that detects a deflection of one or more regions of tissue under an applied stress. Alternatively, a more precise measurement for the biomechanical parameters, including spatial variance in the parameters across the tissue types, can be determined using a device, such as that described in U.S. Published Patent Application No. 2008/0086048, the entire contents of which are herein incorporated by reference, that can be utilized to determine biomechanical properties of the cornea, including non-linear measures of elasticity, at each of a plurality of locations. In this implementation, the data from the imaging system and the elastography data can be used at the FEM component to generate the finite element model of the cornea, including displacements and strains on the corneal tissue from other portions. Alternatively, the parameter measurement system can provide the biomechanical parameters as spatially varying functions of one or more parameters across a portion of the eye (e.g., the cornea and sclera), with the finite element modeling component utilizing the functions to model the biomechanical properties of the tissue. For example, the gradient of a non-linear measures of viscoelasticity, such as hysteresis, stress relaxation, or creep can be determined in one or more directions, and a function describing the change in the nonlinear viscoelasticity can be derived (e.g., via a regression analysis) from the collected data.

Once a geometry for the eye and biomechanical parameters for the tissue have been established, individual parameters for the finite elements comprising the model can be altered by a user at an input device to simulate a particular stiffening process on the eye. The altered model can then be reconciled to calculate an overall shape of the eye, with an emphasis on the cornea and sclera. From the determined shape, one or more optical parameters, such as optical power values and Zernike polynomials characterizing the shape of the cornea, can be determined and provided to the user, along with the calculated shape of the eye at a display. The modeling can be used either for individual patients, to shape a corneal stiffening pattern to the topography of the patient's cornea, or prospectively, to determine appropriate patterns for treatment for patients with eyes having particular characteristics. For example, the model can be used to develop empirical functions that mathematically relate the amount of stiffening to the stiffening agent dosage, penetration depth, exposure time, and a spatial energy profile of any light source required for imparting stiffening. This relationship would allow design of appropriate exposures, through implementation of the finite element model, to customize treatments according to the pattern and magnitude of astigmatism Alternatively, patients can be treated for astigmatism by applying a standard pattern of corneal stiffening. The treatment can be adjusted for a magnitude of the astigmatism or another optical parameter, for example, by increasing an intensity, for example, a dosage, penetration depth, exposure time, or spatial energy profile of any light source required for imparting stiffening of the corneal stiffening treatment. Where additional adjustment is desired, the pattern itself can be parameterized, such that one or more attributes of the pattern can be altered in response to optical properties of the patient's eye. This parameterization can be based, for example, on empirical relationships determined via the finite element model. It will be appreciated, in one implementation, that the pattern can be parameterized individually on both sides of the axis of greater curvature. Accordingly, the treatment can be made asymmetric to correct complex complex astigmatic patterns. For example, an appropriate pattern can be determined via reference to corneal topography, elevation, or elastic property maps.

To this end, FIGS. 2-6 each illustrate an example of a corneal stiffening pattern for treating regular astigmatism. In each of the figures, a vertical axis of greater curvature is shown for the astigmatism, although it will be appreciated that the pattern can be altered for an arbitrarily oriented axis of greater curvature. FIGS. 7-11 each illustrate an example of a corneal stiffening patterns for treating irregular astigmatism. These patterns are based around a skewed hemi-axis model, which assumes that such that the axis of greater curvature forms an oblique angle with a vertex near the center of the eye. For more complex irregularities, it will be appreciated that the patient specific modeling described above could be employed.

The patterns are also selectable to have a corrective effect on other aberrations within the eye, for example, spherical refractive errors. FIGS. 2, 3, 7, and 8 demonstrate patterns likely to provide a lengthening of the optical length of the eye, providing an additional benefit for hyperopic eyes or eyes with particularly flat corneas. FIGS. 4-6 and 9-11 demonstrate patterns likely to provide a shortening of the optical length of the eye, providing an additional benefit for myopic eyes or eyes with particularly steep corneas. FIG. 12 provides a balanced pattern for eyes with little spherical aberration or severe astigmatism. Accordingly, other optical properties of the eye can utilized in the selection and configuration of the stiffening pattern.

Figure 2:
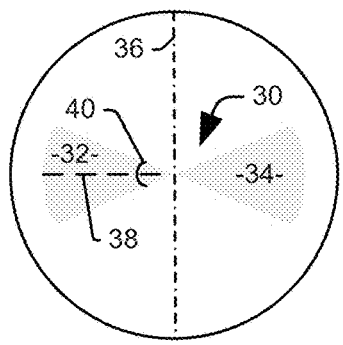
FIGS. 2-6 each illustrate an example of a corneal stiffening pattern for treating regular astigmatism in accordance with an aspect of the present invention.

FIG. 2 illustrates a first example of a corneal stiffening pattern 30 for treating regular astigmatism in accordance with an aspect of the present invention. This pattern is intended to treat astigmatism in excessively flat corneas or hyperopic eyes by steeping the flatter axis of the cornea. The pattern 30 comprises two circular sectors 32 and 34 having apexes at or near the axis of greater curvature 36. Accordingly, very little, and in some implementations, substantially none, of the axis of greater curvature is overlapped by the pattern 30. Although variations are possible to match the specific topography of the cornea and introduce asymmetric effects to treat complex astigmatism, in one implementation, the circular sectors 32 and 34 are effectively mirror images of one another, such that the pattern 30 is substantially symmetrical with respect to the axis of greater curvature.

In accordance with an aspect of the present invention, at least one attribute associated with the pattern 30 can be altered to customize the pattern to an eye of the patient. Specifically, one or both of the radius 38 and the central angle 40 of each circular sector (e.g., 32) can be determined, at least in part, as a function of at least one optical parameter of the patient's eye, such as a magnitude of the astigmatism, one or more Zernike polynomials describing the eye, or prescribed spherical or cylindrical corrections for the eye. Accordingly, even with the use of a standard pattern 30, the treatment can be customized to provide an improve outcome for each patient.

Figure 3:
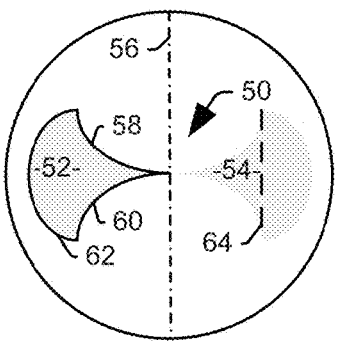

FIG. 3 illustrates a second example of a corneal stiffening pattern 50 for treating regular astigmatism in accordance with an aspect of the present invention. This pattern is intended to treat astigmatism in excessively flat corneas or hyperopic eyes by steeping the flatter axis of the cornea. The pattern 50 comprises two regions 52 and 54, meeting on a point on the axis of greater curvature 56. Each region (e.g., 52) is bounded by two concave curves 58 and 60, having respective first endpoints at the point on the axis of greater curvature, and a third, convex curve 62 extending between respective second endpoints of the two concave curves. Accordingly, very little, and in some implementations, substantially none, of the axis of greater curvature is overlapped by the pattern 50. It will be appreciated, however, that to simplify implementation of the pattern, the two regions 52 and 54 may be connected by a small, continuous region passing through the axis of greater curvature 56 as opposed to meeting at a point on the axis.

Although variations are possible to match the specific topography of the cornea and introduce asymmetric effects to treat complex astigmatism, in one implementation, the regions 52 and 54 are effective mirror images of one another, such that the pattern 50 is substantially symmetrical with respect to the axis of greater curvature. However, in accordance with an aspect of the present invention, at least one attribute associated with the pattern 50 can be altered to customize the pattern to an eye of the patient. Specifically, one or more of the curvatures and lengths of the concave curves 58 and 60, a straight line distance 64 between the second endpoints of the concave curves, and a curvature of the convex curve 62 for each region can be determined, at least in part, as a function of at least one optical parameter of the patient's eye, such as a magnitude of the astigmatism, one or more Zernike polynomials describing the eye, or prescribed spherical or cylindrical corrections for the eye. Accordingly, even with the use of a standard pattern 50, the treatment can be customized to provide an improve outcome for each patient.

Figure 4:
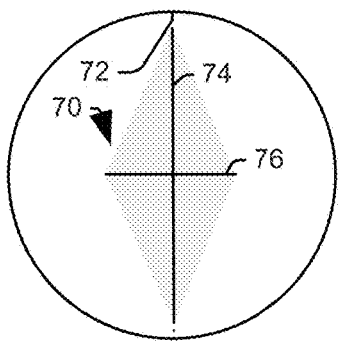

FIG. 4 illustrates a third example of a corneal stiffening pattern 70 for treating regular astigmatism in accordance with an aspect of the present invention. This pattern 70 is intended to treat excessively steep corneas or myopic eyes through selective flattening of the cornea along the axis of greater curvature 72. As a result, this pattern encompasses substantially all of the axis of greater curvature. The pattern 70 is shaped as a parallelogram substantially bisected by the axis of greater symmetry 72 such that a first diagonal 74 of the parallelogram is substantially aligned with the axis of greater symmetry. In accordance with an aspect of the present invention, at least one attribute associated with the pattern 70 can be altered to customize the pattern to an eye of the patient. Specifically, one or both of the length of the first diagonal 74 and a length of the second diagonal 76 can be determined, at least in part, as a function of at least one optical parameter of the patient's eye, such as a magnitude of the astigmatism, one or more Zernike polynomials describing the eye, or prescribed spherical or cylindrical corrections for the eye. Accordingly, even with the use of a standard pattern 70, the treatment can be customized to provide an improve outcome for each patient.

Figure 5:
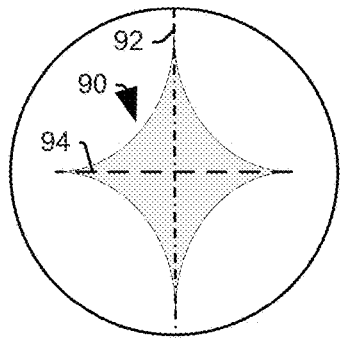

FIG. 5 illustrates a fourth example of a corneal stiffening pattern 90 for treating regular astigmatism in accordance with an aspect of the present invention. This pattern 90 is intended to treat excessively steep corneas or myopic eyes through selective flattening of the cornea along the axis of greater curvature 92. As a result, this pattern encompasses substantially all of the axis of greater curvature. The pattern 90 is bounded by four concave lines to provide a boundary with four cusps, the boundary being aligned such that two cusps of the four cusps of the boundary lie on the axis of greater curvature.

In accordance with an aspect of the present invention, at least one attribute associated with the pattern 90 can be altered to customize the pattern to an eye of the patient. Specifically, one or more of the curvatures and lengths of the four concave lines, and a straight line distance 94 between the cusps not lying on the axis of greater curvature can be determined, at least in part, as a function of at least one optical parameter of the patient's eye, such as a magnitude of the astigmatism, one or more Zernike polynomials describing the eye, or prescribed spherical or cylindrical corrections for the eye. Accordingly, even with the use of a standard pattern 90, the treatment can be customized to provide an improve outcome for each patient.

Figure 6:
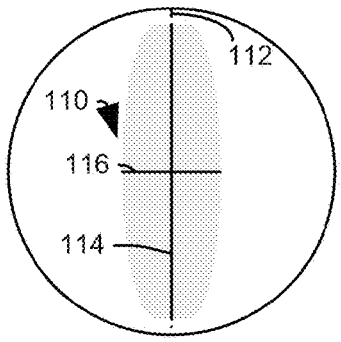

FIG. 6 illustrates a fifth example of a corneal stiffening pattern 110 for treating regular astigmatism in accordance with an aspect of the present invention. This pattern 110 is intended to treat excessively steep corneas or myopic eyes through selective flattening of the cornea along the axis of greater curvature 112. As a result, this pattern encompasses substantially all of the axis of greater curvature. The pattern 110 is substantially elliptical, with the ellipse substantially bisected by the axis of greater symmetry 112 such that major axis 114 of the ellipse is substantially aligned with the axis of greater symmetry. To simplify the patterning, each end of the ellipse along the major axis can be flattened. In accordance with an aspect of the present invention, at least one attribute associated with the pattern 110 can be altered to customize the pattern to an eye of the patient. Specifically, one or both of the length of the major axis 114 and a length of minor axis 116 can be determined, at least in part, as a function of at least one optical parameter of the patient's eye, such as a magnitude of the astigmatism, one or more Zernike polynomials describing the eye, or prescribed spherical or cylindrical corrections for the eye. Accordingly, even with the use of a standard pattern 110, the treatment can be customized to provide an improve outcome for each patient.

Figure 7:
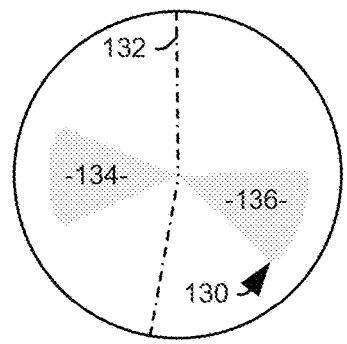
FIGS. 7-11 each illustrate an example of a corneal stiffening pattern for treating irregular astigmatism in accordance with an aspect of the present invention.

FIG. 7 illustrates a first example of a corneal stiffening pattern 130 for treating irregular astigmatism in accordance with an aspect of the present invention. The pattern 130 of FIG. 7 is a modification of the pattern of FIG. 2 to account for the axis of greater curvature 132 taking the form of a skewed hemi-axis. It will be appreciated that the two circular sections 134 and 136 are angled with respect to one another as to account for the bending of the region of greater curvature, such that they remain roughly symmetric around the axis of greater curvature 132. It will be appreciated, however, that for an irregular astigmatism, it is likely that complex astigmatic patterns may be present, such that the radii and the central angles of the circular sections 134 and 136 will likely be different from one another. Alternatively, the intensity of treatment may be varied on opposing sides of the axis of greater curvature, such that the appropriate asymmetric effects can be achieved with an substantially symmetrical pattern.

Figure 8:
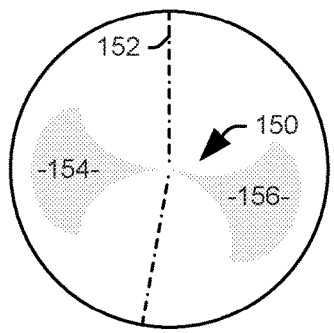

FIG. 8 illustrates a second example of a corneal stiffening pattern 150 for treating irregular astigmatism in accordance with an aspect of the present invention. The pattern 150 of FIG. 8 is a modification of the pattern of FIG. 3 to account for the axis of greater curvature 152 taking the form of a skewed hemi-axis. It will be appreciated that the two regions 154 and 156 are angled with respect to one another as to account for the bending of the region of greater curvature, such that they remain roughly symmetric around the axis of greater curvature 152. Again, given the irregular astigmatism, it is very likely that the parameters defining the pattern, specifically the curvatures and lengths of the concave curves, the straight line distance between the second endpoints of the concave curves, and the curvature of the convex curve will differ between the two regions 154 and 156.

Figure 9:
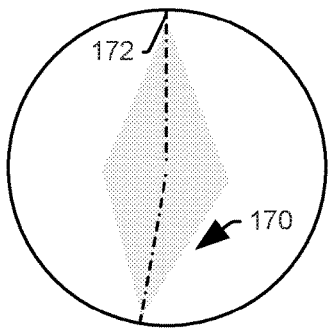

FIG. 9 illustrates a third example of a corneal stiffening pattern 170 for treating irregular astigmatism in accordance with an aspect of the present invention. The pattern 170 of FIG. 9 is a modification of the pattern of FIG. 4 to account for the axis of greater curvature 172 taking the form of a skewed hemi-axis. In the pattern 170, the parallelogram of FIG. 4 has been bent to form an irregular quadrilateral roughly symmetric around the bent axis of greater curvature 172. A shape, area, and intensity of the pattern on either side of the axis of greater curvature 172 can be determined according to one or more mechanical or optical properties of the eye to provide an appropriate correction for the irregular astigmatic pattern.

Figure 10:
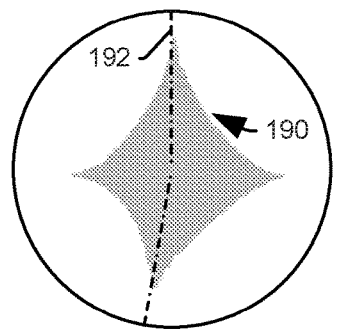

FIG. 10 illustrates a fourth example of a corneal stiffening pattern 190 for treating irregular astigmatism in accordance with an aspect of the present invention. The pattern 190 of FIG. 10 is a modification of the pattern of FIG. 5 to account for the axis of greater curvature 192 taking the form of a skewed hemi-axis. In the pattern 190, the lengths and curvatures of the concave curves bounding the pattern have been altered to maintain a pattern roughly symmetric around the bent axis of greater curvature 192. The curvatures and lengths of the concave curves can be determined according to one or more mechanical or optical properties of the eye to provide an appropriate correction for the irregular astigmatic pattern.

Figure 11:
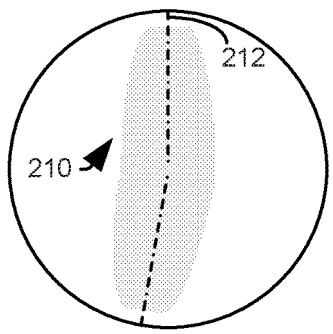
Figure 12:
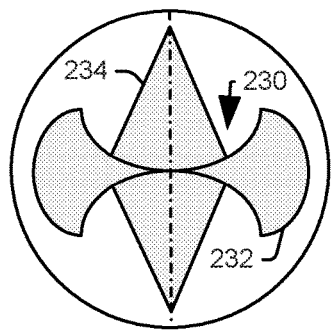
FIG. 12 illustrates an example of a corneal stiffening pattern for eyes with severe astigmatism and/or balanced spherical equivalent effects.

FIG. 11 illustrates a fifth example of a corneal stiffening pattern 210 for treating irregular astigmatism in accordance with an aspect of the present invention. The pattern 210 of FIG. 11 is a modification of the pattern of FIG. 6 to account for the axis of greater curvature 212 taking the form of a skewed hemi-axis. In the illustrated pattern 210, the substantially elliptical pattern of FIG. 6 has been bent to form an irregular curved shape that is roughly symmetric around the bent axis of greater curvature 212. A shape, area, and intensity of the pattern on either side of the axis of greater curvature 212 can be determined according to one or more mechanical or optical properties of the eye to provide an appropriate correction for the irregular astigmatic pattern.

FIG. 12 illustrates an example 230 of a corneal stiffening pattern for eyes with severe astigmatism and/or balanced spherical equivalent effects in accordance with an aspect of the present invention. It will be appreciated that FIG. 12 uses a combination of a first pattern 232 similar to that of FIG. 3 configured to steepen the flat axis of the eye and a second pattern, similar to that of FIG. 4 to flatten the steep axis of the eye. By balancing the relative intensity of stiffening of these two patterns, the effects of spherical aberration in the eye can be controlled. Further, the overall degree of correction for the astigmatism can be greatly enhanced via the combination of the steepening and flattening effects.

Figure 13:
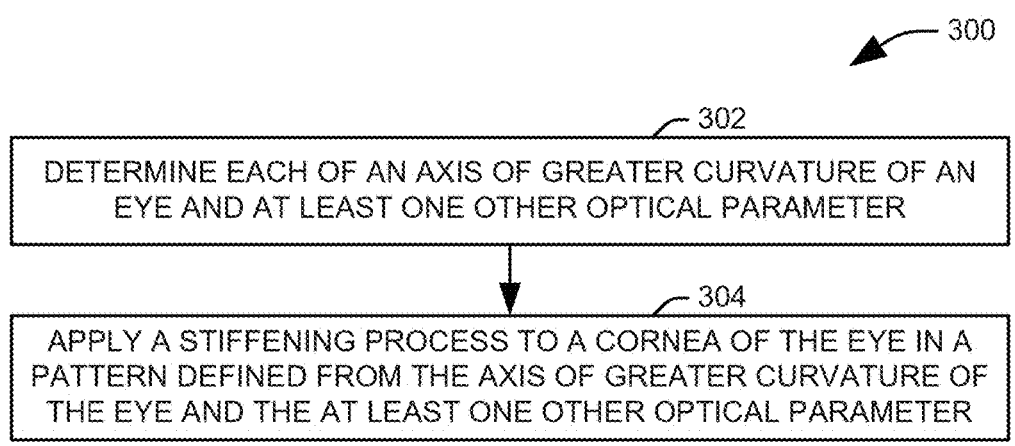
FIG. 13 illustrates another method of treating astigmatism in an eye of a patient in accordance with an aspect of the present invention.

FIG. 13 illustrates another method 300 of treating astigmatism in an eye of a patient in accordance with an aspect of the present invention. At 302, each of an axis of greater curvature of the eye and at least one other optical parameter are determined. For example, the at least one other optical parameter can include a magnitude of the astigmatism, one or more Zernike polynomials describing the eye, prescribed spherical or cylindrical corrections for the eye, or a determination that the patient is significantly myopic, significantly hyperopic, or neither. In one implementation, local elastic strength can be utilized to find targets for treating astigmatism, such that the pattern is defined to selectively stiffen areas of lower elastic strength. In another implementation, the pattern can be defined to selectively stiffen areas of higher elevation.

At 304, a stiffening process is applied to a cornea of the eye in a pattern defined from the axis of greater curvature of the eye and the at least one other optical parameter. For example, the pattern could be selected according to whether the eye significantly myopic or hyperopic, and aligned to be symmetrical around the axis of greater curvature. Alternatively, a selected pattern can be varied according the at least one parameter, such that one or more attributes of the pattern are determined as functions of the at least one parameter. For example, in a first implementation, the defined pattern includes two regions, meeting on a point on the axis of greater curvature. Each region is bounded by two concave curves, having respective first endpoints at the point on the axis of greater curvature, and a third, convex curve extending between respective second endpoints of the two concave curves. A straight-line distance between the second endpoints of the two concave curves for each region can be a function of the at least one other optical parameter. For example, this width could be a function of the magnitude of the astigmatism, such that the pattern is altered to provide additional flattening in the periphery of the cornea is achieved when the steepness is larger.

In a second implementation, the defined pattern includes two regions, meeting on a point on the axis of greater curvature, with each region comprising a circular section having a central angle and a radius. One or both of the central angle and the length of the radius being a function of the at least one other optical parameter. As above, increasing the central angle and the radius increases the flattening effects in the periphery of the cornea, allowing the stiffening treatment to be varied to different corneal topographies. In a third implementation, the pattern is a parallelogram substantially bisected by the axis of greater symmetry such that a first diagonal is substantially aligned with the axis of greater symmetry. A width of a second diagonal can a function of the at least one other optical parameter, such that a flattening along the axis of greater curvature can be increased or decreased according to the optical properties of the patient's eye.

In a fourth implementation, the pattern is substantially elliptical, with a length of a minor axis of the elliptical pattern being a function of the at least one other optical parameter. In a fifth implementation, the defined pattern is bounded by four concave lines to provide a boundary with four cusps. The boundary being aligned such that two cusps of the four cusps of the boundary lie on the axis of greater curvature, with a distance between an other two cusps of four boundary cusps being a function of the at least one other optical parameter. In both of these implementations, controlling these parameters allows a width of the pattern around the axis of greater curvature to be controlled, such that the flattening effect at the axis can be varied on a patient-specific basis. Accordingly, even using standard patterns, the treatment can be customized to the needs of individual patients.

Figure 14:
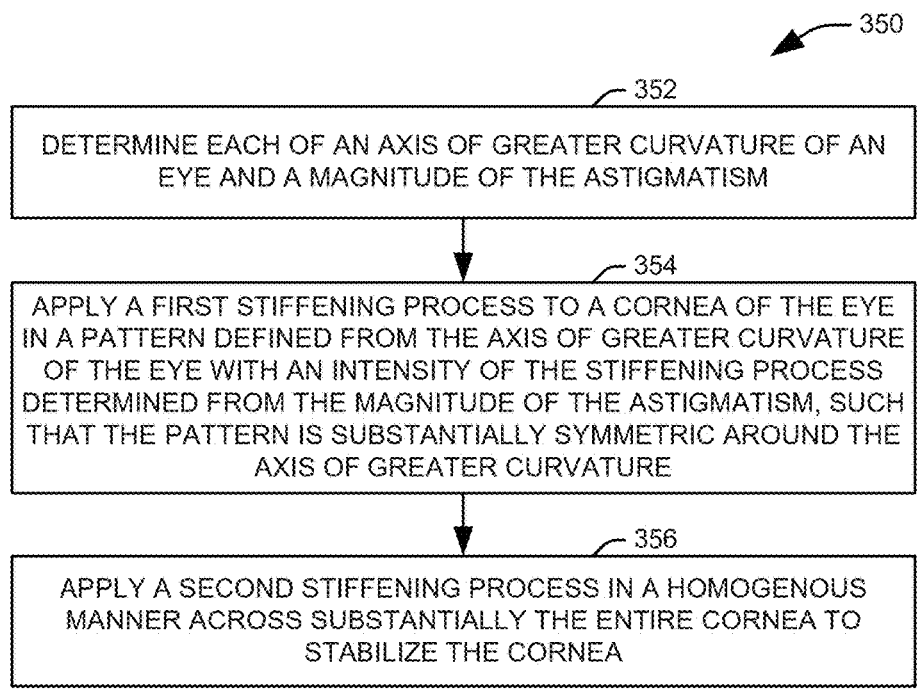
FIG. 14 illustrates yet another method of treating astigmatism in an eye of a patient in accordance with an aspect of the present invention.

FIG. 14 illustrates yet another method 350 of treating astigmatism in an eye of a patient in accordance with an aspect of the present invention. At 352, each of an axis of greater curvature of the eye and a magnitude of the astigmatism is determined. At 354, a first stiffening process is applied to a cornea of the eye in a pattern defined from the axis of greater curvature of the eye and an intensity determined from the magnitude of the astigmatism. The pattern is applied as to be substantially symmetrical around the axis of greater curvature. At 356, a second stiffening process is applied in a homogenous manner across substantially the entire cornea to stabilize the cornea after the first stiffening process.

What have been described above are examples of the present invention. It is, of course, not possible to describe every conceivable combination of components or methodologies for purposes of describing the present invention, but one of ordinary skill in the art will recognize that many further combinations and permutations of the present invention are possible. Accordingly, the present invention is intended to embrace all such alterations, modifications, and variations that fall within the scope of the appended claims.

What is claimed is:

1. A method for treating astigmatism in an eye of a patient comprising:
   determining each of an axis of greater curvature of the eye and a magnitude of the astigmatism;
   applying a first stiffening process to a cornea of the eye in a pattern defined from the axis of greater curvature of the eye and with an intensity defined from the magnitude of the astigmatism, the pattern being substantially symmetrical around the axis of greater curvature; and
   applying a second stiffening process in a homogenous manner across substantially the entire cornea to stabilize the cornea after the first stiffening process.

* * * * *

UNITED STATES PATENT AND TRADEMARK OFFICE
CERTIFICATE OF CORRECTION

PATENT NO. : 10,398,763 B2  
APPLICATION NO. : 14/165796  
DATED : September 3, 2019  
INVENTOR(S) : William J. Dupps et al.

Page 1 of 1

It is certified that error appears in the above-identified patent and that said Letters Patent is hereby corrected as shown below:

In the Specification

Column 1, Line 10, please add new language before TECHNICAL FIELD as follows:
This invention was made with government support under EY023381 awarded by the National Institutes of Health. The government has certain rights in the invention.

Signed and Sealed this
Fifth Day of April, 2022

Drew Hirshfeld
*Performing the Functions and Duties of the*
*Under Secretary of Commerce for Intellectual Property and*
*Director of the United States Patent and Trademark Office*